United States Patent [19]

Berrer et al.

[11] 4,436,935
[45] Mar. 13, 1984

[54] THIOCARBAMOYLALKOXY-PHENYLUREAS

[75] Inventors: Dagmar Berrer, Riehen, Switzerland; Georg Pissiotas, Lörrach, Fed. Rep. of Germany; Otto Rohr, Therwil, Switzerland

[73] Assignee: Ciba-Geigy Corporation, Ardsley, N.Y.

[21] Appl. No.: 291,008

[22] Filed: Aug. 7, 1981

[30] Foreign Application Priority Data

Aug. 19, 1980 [CH] Switzerland ............... 6254/80

[51] Int. Cl.³ .................. C07C 161/00; E05B 65/00
[52] U.S. Cl. .......................... 564/49; 71/94; 71/95; 71/100; 71/92; 71/88; 544/165
[58] Field of Search ........... 564/49, 51; 71/98, 120

[56] References Cited

U.S. PATENT DOCUMENTS

| | | | |
|---|---|---|---|
| 3,326,663 | 6/1967 | Soloway et al. | 564/49 |
| 3,746,741 | 7/1973 | Hubele | 71/120 |
| 3,852,348 | 12/1974 | Teach | 564/49 |
| 3,864,395 | 2/1975 | Martin et al. | 564/49 |
| 3,867,426 | 2/1975 | Olin et al. | 564/51 |
| 4,294,986 | 10/1981 | Spoty et al. | 564/49 |

FOREIGN PATENT DOCUMENTS 16731 10/1980 European Pat. Off. .

OTHER PUBLICATIONS

Houben–Weyl, Methoden der Organische Chemie, vol. 8, pp. 672–673 (4th Ed.).

*Primary Examiner*—James H. Reamer
*Attorney, Agent, or Firm*—Frederick H. Rabin

[57] ABSTRACT

The invention relates to thiocarbamoylalkoxyphenylureas of the general formula

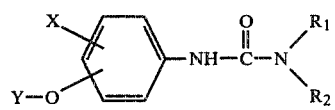

wherein
X is hydrogen, halogen, $C_1$–$C_2$haloalkoxy or $C_1$–$C_2$haloalkyl,
Y is a thiocarbamoylalkyl group of the formula

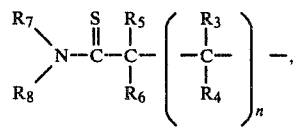

n is 0, 1 or 2,
$R_1$ is hydrogen, $C_1$–$C_4$alkyl, $C_2$–$C_4$alkenyl, $C_2$–$C_4$alkynyl or $C_1$–$C_4$alkoxy,
$R_2$ is hydrogen, $C_1$–$C_4$alkyl or $C_2$–$C_4$alkenyl,
$R_3$, $R_4$ and $R_6$, each independently or the other, are hydrogen or $C_1$–$C_4$alkyl,
$R_5$ is hydrogen, $C_1$–$C_4$alkyl, $C_1$–$C_4$alkoxy or $C_2$–$C_5$alkoxyalkyl,
$R_7$ is hydrogen, $C_1$–$C_4$alkyl, $C_2$–$C_4$alkenyl, $C_2$–$C_4$alkynyl, $C_1$–$C_4$alkoxy or $C_1$–$C_2$alkylphenyl, and
$R_8$ is hydrogen or $C_1$–$C_4$alkyl, while $R_1$ and $R_2$ or $R_7$ and $R_8$, together with the nitrogen atom to which they are attached, can form a 5- or 6-membered heterocyclic ring system which can be interrupted by further hetero-atoms.

These compounds have excellent selective herbicidal and plant growth inhibiting properties.

5 Claims, No Drawings

THIOCARBAMOYLALKOXYPHENYLUREAS

The present invention relates to novel thiocarbamoylalkoxyphenylureas having selective herbicidal action, to the production thereof, to compositions containing them, and to the use thereof for controlling weeds in crops of useful plants such as soybeans, cotton, cereals, maize, millet and rice.

The thiocarbamoylalkoxyphenylureas of this invention have the general formula

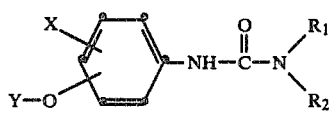

wherein

X is hydrogen, halogen, $C_1$-$C_2$haloalkoxy or $C_1$-$C_2$haloalkyl,

Y is a thiocarbamoylalkyl group of the formula

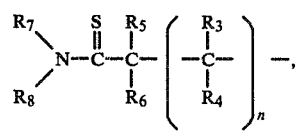

n is 0, 1 or 2, $R_1$ is hydrogen, $C_1$-$C_4$alkyl, $C_2$-$C_4$alkenyl, $C_2$-$C_4$alkynyl or $C_1$-$C_4$alkoxy, $R_2$ is hydrogen, $C_1$-$C_4$alkyl or $C_2$-$C_4$alkenyl, $R_3$, $R_4$ and $R_6$ each independently of the other, are hydrogen or $C_1$-$C_4$alkyl, $R_5$ is hydrogen, $C_1$-$C_4$alkyl, $C_1$-$C_4$alkoxy or $C_2$-$C_5$alkoxyalkyl, $R_7$ is hydrogen, $C_1$-$C_4$alkyl, $C_2$-$C_4$alkenyl, $C_2$-$C_4$alkynyl, $C_1$-$C_4$alkoxy or $C_1$-$C_2$alkylphenyl, and $R_8$ is hydrogen or $C_1$-$C_4$alkyl, whilst $R_1$ and $R_2$ or $R_7$ and $R_8$, together with the nitrogen atom to which they are attached, can form a 5- or 6-membered heterocyclic ring system which can be interrupted by further heteroatoms.

X as halogen denotes fluorine, chlorine or bromine, preferably fluorine, but with chlorine being most preferred.

Alkyl is e.g. methyl, ethyl, n-propyl, isopropyl and the four isomeric butyl radicals, with methyl or ethyl being preferred.

Alkoxy radicals are e.g. methoxy, ethoxy, n-propyloxy, isopropyloxy or tert-butyloxy.

By analogy, haloalkyl and haloalkoxy radicals will be generally understood to denote fluoromethyl, fluoromethoxy, chloromethyl, α-chloroethyl, β-chloroethyl, trifluoromethyl, trifluoromethoxy, α,α,β,β-tetrachloroethyl or β,β,γ,γ-tetrafluoropropyl, with chloromethyl, trifluoromethyl or trifluoromethoxy being preferred.

Alkenyl is e.g. vinyl, allyl, methallyl or crotyl, with vinyl or allyl being preferred.

Alkynyl is ethynyl and, in particular, propargyl.

Examples of possible nitrogen-containing heterocyclic ring systems are pyrrolidine, pyrroline, imidazolidine, pyrazolidine, piperidine, piperazine, morpholine, pyrazoline, imidazole, pyrrole or imidazoline, with pyrrolidine, piperidine or morpholine being preferred.

Preferred compounds on account of their herbicidal action are the compounds of formula I, in which the substituent Y—O— is in the meta- or para-position of the phenyl nucleus. Within this group of compounds, those compounds in which Y—O— is in the meta-position of the phenyl nucleus are especially preferred.

Preference further attaches to compounds of the formula I, in which n is 0, and also to those in which X is hydrogen or halogen.

The most preferred compounds, however, are the compounds of formula I, in which Y—O— is in the meta-position of the phenyl nucleus, n is 0, each of X, $R_7$ and $R_8$ is hydrogen, $R_2$ is methyl, and $R_1$ is methoxy or methyl.

The compounds of formula I are obtained by methods which are known per se.

Accordingly, the thiocarbamoyl compounds of formula I are obtained by a process similar to one described in Houben-Weyl, Methoden der organischen Chemie, 4th Ed., Vol. 8, page 672, by reacting a carboxylic acid nitrile of the formula II

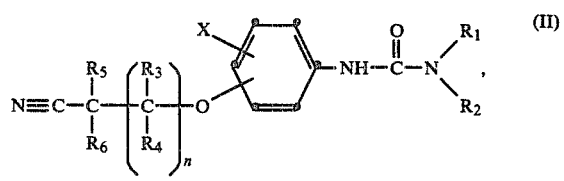

wherein X, n, and $R_1$ to $R_6$ are as defined for formula I, if desired in the presence of a catalyst, with hydrogen sulfide.

If desired, the thiocarboxamides can be converted by generally known methods into the N-substituted amides.

The reactions are conducted in inert organic solvents, e.g. methanol, ethanol, tetrahydrofurane, dioxane, diethyl ether, benzene, pyridine and toluene, at room temperature and under normal pressure. It can also be advantageous to carry out the reaction in liquified hydrogen sulfide, at elevated temperature (30°–150° C.), in an autoclave.

Catalysts which may be used with advantage are basic catalysts, e.g. ammonium bisulfides or alkali bisulfides, and also organic bases such as diethylamine, triethylamine, piperidine, pyrrolidine, pyridine, morpholine, quinolidine and 4-dimethylaminopyridine.

The starting compounds of the formula II can be obtained by the process described in European patent application No. 80810090.3.

Thus, for example, the starting compounds of the formula II are obtained by reacting an appropriately substituted phenyl compound of the formula III

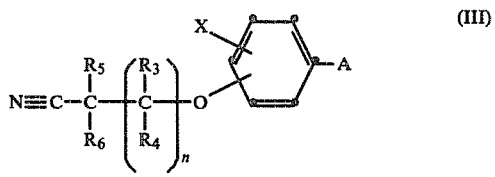

with an amine of the formula IV

In the formulae III and IV above, X, n, and $R_1$ to $R_6$ are as defined for formula I, whilst A and Z are radicals which form ureas by addition or condensation. One of the radicals A and Z is an amine, and the other is an alkoxycarbonyl, haloformyl or carbamoyl group, or, in particular, the isocyanato radical.

The starting materials are also obtained by reacting hydroxyphenylureas of the formula V

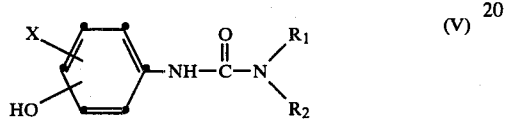

with cyanoalkylhalides of the formula VI

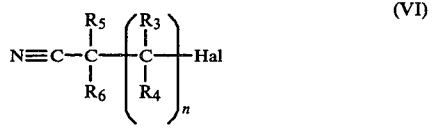

in the presence of an acid acceptor.

In the formulae V and VI above, X, N, and $R_1$ to $R_6$ are as defined for formula I, and Hal is chlorine or bromine.

The novel compounds of the formula I are stable compounds which are soluble in conventional organic solvents such as alcohols, ethers, ketones, dimethyl formamide and dimethyl sulfoxide.

The compounds of the formula I have, in general, pronounced selective herbicidal properties, and are particularly advantageous for controlling weeds both pre- and postemergence in crops of useful plants, especially in soybeans, cotton, cereals, maize, millet and rice.

When applied postemergence, the compounds of formula I have selective herbicidal action against a number of monocot weeds. Excellent results are obtained, however, against dicots in postemergence application. Accordingly, the principal field of use in the postemergence control of dicot weeds, in particular of individual problem weeds such as Galium aparine.

It is especially noteworthy that the growth of cereals such as corn and barley is insignificantly impaired, and that of maize and millet hardly at all. A good selective action against dicot weeds in soybeans can also be achieved by careful application of compounds of the formula I.

No protective measures are required for handling the compounds of formula I. They can be formulated as liquid herbicidal compositions only with the aid of conventional solubilisers and/or dispersants.

The compositions of the present invention are obtained in known manner by intimately mixing and grinding compounds (active ingredients) of the general formula I with suitable carriers and/or adjuvants, if appropriate with the addition of antifoams, wetting agents, dispersants and/or solvents which are inert to the active ingredients. The active ingredients can be processed to the following formulations:

solid formulations: dusts, tracking powders, granules (coated granules, impregnated granules and homogenous granules);

active ingredient concentrates which are dispersible in water: wettable powders, pastes, emulsions, emulsifiable concentrates;

liquid formulations: solutions.

The concentrations of active ingredient in the composition of this invention are between 1 and 80 percent by weight. As circumstances may require, the active ingredients can also be applied in low concentrations of about 0,05 to 1% by weight. The rates of application can vary within wide limits, e.g. from 0.1 to 10 kg, preferably from 0.5 to 5 kg, of active ingredient per hectare.

To broaden the activity spectrum or to achieve a desired synergistic or antagonistic effect, these compounds can also be employed together with known herbicidal, insecticidal, nematocidal, bactericidal, acaricidal or fungicidal compounds, for example the preparations described in the "Pesticidal Manual", 6th Edition, The British Crop Protection Council, ISBN 0-901 436-44-5.

In the following Examples, parts and percentages are by weight.

EXAMPLE 1

α-[m-(3-Methoxy-3-methylureido)phenoxy]thiopropionamide

With stirring and cooling to 20°–30° C., a stream of hydrogen sulfide is passed for 1 hour through a mixture of 17.5 g of α-[m-(3-methoxy-3-methylureidophenoxy]-propionitrile, 24 g of pyridine and 7 g of triethylamine. The reaction mixture is then poured into water and extracted with ethyl acetate. The organic phase is dried and concentrated, and the residue is crystallised from ethanol/water, affording 12.3 g of α[m-(3-methoxy-3-methylureido)phenoxy]thiopropionamide with a melting point of 95°–96° C. (compound 2).

The following table lists compound 2 of this Example and thiocarbamoylphenylureas of the formula I which are synthesized in similar manner.

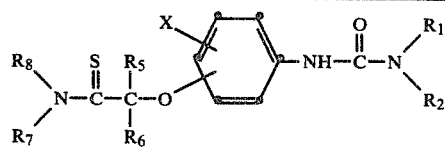

| No. | X | $R_1, R_2$ | $R_5$ | $R_6$ | $R_7, R_8$ | Position of the thiocarbamoyl-alkoxy radical | Physical data (°C.) |
|---|---|---|---|---|---|---|---|
| 1 | H | $CH_3, CH_3$ | H | H | H, H | 3 | m.p. 166° |
| 2 | H | $OCH_3, CH_3$ | $CH_3$ | H | H, H | 3 | m.p. 95–96° |
| 3 | H | $CH_3, CH_3$ | $CH_3$ | H | H, H | 3 | m.p. 1,5839 |
| 4 | H | $CH_3, CH_3$ | $C_2H_5$ | H | H, H | 3 | m.p. 62° |
| 5 | H | $OCH_3, CH_3$ | $C_2H_5$ | H | H, H | 3 | m.p. 123° |
| 6 | H | $C_4H_9n, H$ | $CH_3$ | H | $C_4H_9n, H$ | 3 | m.p. 1,5539 |
| 7 | 3-Cl | $CH_3, CH_3$ | $CH_3$ | H | H, H | 4 | m.p. 180–181° |
| 8 | 3-Cl | $CH_3, CH_3$ | H | H | H, H | 4 | m.p. 175–176° |
| 9 | 3-Cl | $OCH_3CH_3$ | H | H | H, H | 4 | m.p. 173–174° |
| 10 | 3-Cl | $CH_3, CH_3$ | $C_2H_5$ | H | H, H | 4 | m.p. 175° |
| 11 | 3-Cl | $OCH_3, CH_3$ | $CH_3$ | H | H, H | 4 | m.p. 186–187° |
| 12 | H | $OCH_3, CH_3$ | $H_3$ | H | H, H | 4 | m.p. 185° |
| 13 | H | $CH_3, CH_3$ | $CH_3$ | H | H, H | 4 | m.p. 174–175° |
| 14 | H | $CH_3, CH_3$ | H | H | H, H | 4 | m.p. 181–182° |
| 15 | 3-Cl | $OCH_3, CH_3$ | $C_2H_5$ | H | H, H | 4 | m.p. 184–185° |
| 16 | H | $OCH_3, CH_3$ | $C_2H_5$ | H | H, H | 4 | m.p. 136–137° |
| 17 | H | $OCH_3, CH_3$ | $CH_3$ | H | $CH_3, H$ | 3 | m.p. 97–98° |
| 18 | H | $OCH_3, CH_3$ | $CH_3$ | H | $C_2H_5, H$ | 3 | oil |
| 19 | H | $OC_3, CH_3$ | $CH_3$ | H | $C_3H_7n, H$ | 3 | m.p. 133–134° |
| 20 | H | $OCH_3, CH_3$ | $CH_3$ | H | $C_3H_7i, H$ | 3 | |
| 21 | H | $OCH_3, CH_3$ | $CH_3$ | H | $C_4H_9n, H$ | 3 | $n_D^{39}$: 1.5586 |
| 22 | H | $OCH_3, CH_3$ | $CH_3$ | H | $C_4H_9i, H$ | 3 | |
| 23 | H | $OCH_3, CH_3$ | $CH_3$ | H | $C_4H_9s, H$ | 3 | |
| 24 | H | $OCH_3, CH_3$ | $CH_3$ | H | $C_4H_9t, H$ | 3 | |
| 25 | H | $OCH_3, CH_3$ | $CH_3$ | H | $-CH_2-CH=CH_2, H$ | 3 | |
| 26 | H | $OCH_3, CH_3$ | $CH_3$ | H | $CH_3, CH_3$ | 3 | |
| 27 | H | $OCH_3, CH_3$ | $CH_3$ | H | $OCH_3, CH_3$ | 3 | |
| 28 | H | $OCH_3, CH_3$ | $CH_3$ | H | $C_4H_9n, CH_3$ | 3 | |
| 29 | H | $OCH_3, CH_3$ | $CH_3$ | H | $C_4H_9n, C_4H_9n$ | 3 | |
| 30 | H | $OCH_3, CH_3$ | $CH_3$ | H | $C_2H_5, C_2H_5$ | 3 | |
| 31 | H | $OCH_3, CH_3$ | $CH_3$ | H | $-(CH_2)_2-O-(CH_2)_2-$ | 3 | |
| 32 | H | $OCH_3, CH_3$ | $CH_3$ | H | $-CH_2-CH(O-(CH_2)_2)-CH_3$ | 3 | |
| 33 | H | $OCH_3, CH_3$ | $CH_3$ | H | $-CH(CH_3)-C\equiv CH, CH_3$ | 3 | |
| 34 | H | $CH_3, CH_3$ | $CH_3$ | H | $CH_3, H$ | 3 | m.p. 117–118° |
| 35 | H | $CH_3, CH_3$ | $CH_3$ | H | $C_2H_5 H$ | 3 | m.p. 107–108° |
| 36 | H | $CH_3, CH_3$ | $CH_3$ | H | $C_3H_7n, H$ | 3 | m.p. 91–92° |
| 37 | H | $CH_3, CH_3$ | $CH_3$ | H | $C_3H_7i, H$ | 3 | m.p. 133–134° |
| 38 | H | $CH_3, CH_3$ | $CH_3$ | H | $C_4H_9n, H$ | 3 | |
| 39 | H | $CH_3, CH_3$ | $CH_3$ | H | $C_4H_9i, H$ | 3 | |
| 40 | H | $CH_3, CH_3$ | $CH_3$ | H | $C_4H_9s, H$ | 3 | |
| 41 | H | $CH_3, CH_3$ | $CH_3$ | H | $C_4H_9t, H$ | 3 | |
| 42 | H | $CH_3, CH_3$ | $CH_3$ | H | $C_2H_4OCH_3, H$ | 3 | m.p. 101–105° |
| 43 | H | $CH_3, CH_3$ | $CH_3$ | H | $CH_3, CH_3$ | 3 | |
| 44 | H | $CH_3, CH_3$ | $CH_3$ | H | $OCH_3, CH_3$ | 3 | |
| 45 | H | $CH_3, CH_3$ | $CH_3$ | H | $C_4H_9n, CH_3$ | 3 | |
| 46 | H | $CH_3, CH_3$ | $CH_3$ | H | $C_2H_5, C_2H_5$ | 3 | |
| 47 | H | $CH_3, CH_3$ | $CH_3$ | H | $-CH(CH_3)-C\equiv CH, CH_3$ | 3 | |
| 48 | H | $CH_3, H$ | $CH_3$ | H | H, H | 3 | |
| 49 | H | $CH_3, H$ | $CH_3$ | H | $C_4H_9t, H$ | 3 | |
| 50 | H | $CH_3, H$ | $CH_3$ | H | $C_4H_9i, H$ | 3 | |
| 51 | H | $-CH(CH_3)-C\equiv CH, CH_3$ | $CH_3$ | H | H, H | 3 | |
| 52 | H | $C_4H_9n, CH_3$ | $CH_3$ | H | H, H | 3 | |
| 53 | H | $CH_3, C_3$ | $CH_3$ | H | $-(CH_2)_5-$ | 3 | |
| 54 | H | $CH_3, CH_3$ | $CH_3$ | H | $-(CH_2)_4-$ | 3 | |
| 55 | H | $CH_3, CH_3$ | $CH_3$ | H | $-CH_2-CH(CH_3)-O-CH_2-CH(CH_3)-$ | 3 | |
| 56 | H | $OCH_3, CH_3$ | $C_2H_5$ | H | $CH_3, H$ | 3 | m.p. 111–112° |
| 57 | H | $OCH_3, CH_3$ | $C_2H_5$ | H | $C_2H_5, H$ | 3 | resin |
| 58 | H | $OCH_3, CH_3$ | $C_2H_5$ | H | $C_3H_7n, H$ | 3 | |
| 59 | H | $OCH_3, CH_3$ | $C_2H_5$ | H | $C_3H_7i, H$ | 3 | |

-continued

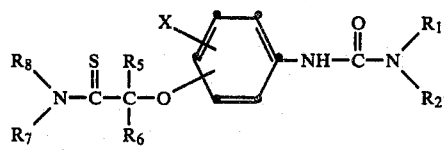

| No. | X | R1, R2 | R5 | R6 | R7, R8 | Position of the thiocarbamoyl-alkoxy radical | Physical data (°C.) |
|---|---|---|---|---|---|---|---|
| 60 | H | OCH3, CH3 | C2H5 | H | C4H9n, H | 3 | |
| 61 | H | OCH3, CH3 | C2H5 | H | C4H9i, H | 3 | |
| 62 | H | OCH3, CH3 | C2H5 | H | C4H9s, H | 3 | |
| 63 | H | OCH3i, CH3 | C2H5 | H | C4H9t, H | 3 | |
| 64 | H | OCH3, CH3 | C2H5 | H | —CH2—CH=CH2, H | 3 | |
| 65 | H | OCH3, CH3 | C2H5 | H | CH3, CH3 | 3 | |
| 66 | H | OCH3, CH3 | C2H5 | H | OCH3, CH3 | 3 | |
| 67 | H | OCH3, CH3 | C2H5 | H | C4H9n, CH3 | 3 | |
| 68 | H | OCH3, CH3 | C2H5 | H | C4H9n, C4H9n | 3 | |
| 69 | H | OCH3, CH3 | C2H5 | H | C2H5, C2H5 | 3 | |
| 70 | H | OCH3, CH3 | C2H5 | H | —(CH2l)2—O—(CH2)2— | 3 | |
| 71 | H | OCH3, CH3 | C2H5 | H | —CH2—CH—CH3 \ O —(CH2)2 | 3 | |
| 72 | H | OCH3, CH3 | C2H5 | H | —CH(CH3)—C≡CH, CH3 | 3 | |
| 73 | H | CH3, CH3 | C2H5 | H | CH3, H | 3 | |
| 74 | H | CH3, CH3 | C2H5 | H | C2H5, H | 3 | |
| 75 | H | CH3, CH3 | C2H5 | H | C3H7n, H | 3 | |
| 76 | H | CH3, CH3 | C2H5 | H | C3H7i, H | 3 | |
| 77 | H | CH3, CH3 | C2H5 | H | C4H9, H | 3 | |
| 78 | H | CH3, CH3 | C2H5 | H | C4H9i, H | 3 | |
| 79 | H | CH3, CH3 | C2H5 | H | C4H9s, H | 3 | |
| 80 | H | CH3, CH3 | C2H5 | H | C4H9t, H | 3 | |
| 81 | H | CH3, CH3 | C2H5 | H | —CH2—CH=CH2, H | 3 | |
| 82 | H | CH3, CH3 | C2H5 | H | CH3, CH3 | 3 | |
| 83 | H | CH3, CH3 | C2H5 | H | OCH3, CH3 | 3 | |
| 84 | H | CH3, CH3 | C2H5 | H | C4H9n, CH3 | 3 | |
| 85 | H | CH3, CH3 | C2H5 | H | C2H5, C2H5 | 3 | |
| 86 | H | CH3, CH3 | C2H5 | H | —CH(CH3)—C≡CH, CH3 | 3 | |
| 87 | H | CH3, H | C2H5 | H | H, H | 3 | |
| 88 | H | CH3, H | C2lH5 | H | C4H9t, H | 3 | |
| 89 | H | CH3, H | C2H5 | H | C4H9i, H | 3 | |
| 90 | H | —CH(CH3)—C≡CH, CH3 | C2H5 | H | H, H | 3 | |
| 91 | H | C4H9n, CH3 | C2H5 | H | H, H | 3 | |
| 92 | H | CH3, CH3 | C2H5 | H | —(CH2)5— | 3 | |
| 93 | H | CH3, CH3 | C2H5 | H | —(CH2)4— | 3 | |
| 94 | H | CH3, CH3 | C2H5 | H | —CH2—CH—CH3 \ O —CH2—CH—CH3 | 3 | |
| 95 | H | CH3, CH3 | C3H7n | H | H, H | 3 | |
| 96 | H | OCH3, CH3 | C3H7n | H | H, H | 3 | m.p.: 86–87° |
| 97 | H | CH3, CH3 | C3H7n | H | C4H9n, H | 3 | |
| 98 | H | CH3, CH3 | C3H7n | H | CH3, H | 3 | m.p.: 132–134° |
| 99 | H | OCH3, CH3 | C3H7n | H | C4H9n, H | 3 | |
| 100 | H | OCH3, CH3 | C3H7n | H | CH3, H | 3 | m.p.: 107–110° |
| 101 | 3-CF3 | CH3, CH3 | CH3 | H | H, H | 4 | m.p.: 179–180° |
| 102 | 3-CF3 | OCH3, CH3 | CH3 | H | H, H | 4 | m.p.: 178–180° |
| 103 | H | CH3, CH3 | C2H5 | H | H, H | 4 | m.p.: 168–169° |
| 104 | H | CH3, CH3 | CH3 | CH3 | H, H | 3 | m.p.: 89–90° |
| 105 | H | OCH3, CH3 | CH3 | CH3 | H, H | 3 | m.p.: 143–144° |
| 106 | H | OCH3, CH3 | C2H5 | H | H, H | 4 | |
| 107 | H | OCH3, CH3 | H | H | H, H | 4 | m.p.: 154–155° |
| 108 | H | OCH3, CH3 | C3H7n | H | H H | 3 | m.p. 86–87° |
| 109 | H | CH3, CH3 | H | H | H H | 4 | m.p. 154–155° |
| 110 | H | OCH3, CH3 | C3H7i | H | H H | 3 | m.p. 1.5822 |
| 111 | H | OCH3, CH3 | H | H | H H | 3 | m.p. 180° |
| 112 | H | OCH3, CH3 | CH3 | CH3 | CH3 H | 3 | m.p. 94–95° |
| 113 | 4-Cl | OCH3 CH3 | CH3 | H | C2H5 H | 3 | m.p. 114–116° |
| 114 | 4-Cl | CH3, CH3 | CH3 | H | CH3 H | 3 | m.p. 94–95° |
| 115 | 3-Cl | OCH3, CH3 | H | H | △ H | 4 | m.p. 136–138° |

-continued

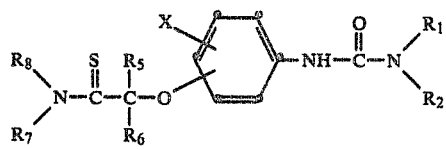

| No. | X | $R_1, R_2$ | $R_5$ | $R_6$ | $R_7, R_8$ | Position of the thiocarbamoyl-alkoxy radical | Physical data (°C.) |
|---|---|---|---|---|---|---|---|
| 116 | 3-Cl | $OCH_3, CH_3$ | $CH_3$ | H | $CH_3$ H | 4 | m.p. 119–120° |
| 117 | 3-Cl | $CH_3, CH_3$ | $CH_3$ | H | $C_2H_4OCH_3$ H | 4 | m.p. 67–71° |
| 118 | 3-$CF_3$ | $CH_3, CH_3$ | $C_2H_5$ | H | H H | 4 | m.p. 160–162° |
| 119 | 3-$CF_3$ | $OCH_3 CH_3$ | $C_2H_5$ | H | H H | 4 | m.p. 160–162° |
| 120 | 3-$CF_3$ | $CH_3 CH_3$ | $CH_3$ | H | $CH_3$ H | 4 | m.p. 157–161° |

EXAMPLE 2

Wettable Powder

The following constituents are used to formulate (a) a 70% and (b) a 10% wettable powder:

(a)
- 70 parts of m-(3,3-dimethylureido)phenoxythioacetamide,
- 5 parts of sodium dibutylnaphthylsulfonate,
- 3 parts of naphthalenesulfonic acid/phenolsulfonic acid/formaldehyde condensate (3:2:1),
- 10 parts of kaolin,
- 12 parts of Champagne chalk;

(b)
- 10 parts of the above compound,
- 3 parts of a mixture of the sodium salts of saturated fatty alcohol sulfates,
- 5 parts of naphthalenesulfonic acid/formaldehyde condensate,
- 83 parts of kaolin.

The active ingredient is applied to the corresponding carriers (kaolin and chalk) and then these are mixed and ground, to yield wettable powders of excellent wettability and suspension powder. By diluting these wettable powders with water it is possible to obtain suspensions containing 0.1 to 80% of active ingredient. These suspensions are suitable for controlling weeds in cultivations of plants.

EXAMPLE 3

Paste

The following substances are used to formulate a 45% paste:
- 45 parts of α[m-(3-methyl-3-methoxyureido)phenoxy]thiopropionamide,
- 5 parts of sodium aluminium silicate,
- 14 parts of cetyl polyglycol ether with 8 moles of ethylene oxide,
- 1 part of oleyl polyglycol ether with 5 moles of ethylene oxide,
- 2 parts of spindle oil,
- 10 parts of polyethylene glycol,
- 23 parts of water.

The active ingredient is intimately mixed with the adjuvants in appropriate devices and ground. By diluting the resultant paste with water, it is possible to prepare suspensions of the desired concentration.

EXAMPLE 4

Emulsifiable Concentrate

The following ingredients are mixed to formulate a 25% emulsifiable concentrate:
- 25 parts of α-[m-(3-methoxy-3-methylureido)phenoxy]thiopropionamide,
- 5 parts of a mixture of nonylphenolpolyoxyethylene and calcium dodecylbenzenesulfonate,
- 15 parts of cyclohexanone,
- 55 parts of xylene.

This concentration can be diluted with water to give emulsions in suitable concentrations of e.g. 0.1 to 10%. Such emulsions are suitable for controlling weeds in crops of cultivated plants.

Flowable preparation

The following substances are used to produce a 45% flowable preparation:
- 45 parts of α-[m-(3,3-dimethylureido)phenoxy]-n-thiobutyramide,
- 5 parts of ethylene glycol,
- 3 parts of octylphenoxypolyethylene glycol having 9–10 moles of ethylene oxide per mole of octylphenol,
- 3 parts of a mixture of aromatic sulfonsulfonic acids, condensed with formaldehyde as ammonium salt,
- 1 part of silicone oil in the form of a 75% emulsion,
- 0.1 part of a mixture of 1-(3-chloroallyl)-3,5,7-triazoazonium-adamantane chloride with sodium carbonate, chloride value at least 11.5%,
- 0.2 part of a bipolymeric thickener having a maximum of 100 nuclei per gram, and
- 42.7 parts of water.

The active ingredient is mixed with the adjuvants in appropriate devices and the mixture is ground. Suspensions of the desired concentration can be obtained by diluting the resultant paste with water.

Biological Examples

EXAMPLE 6

Preemergence herbicidal action

In a greenhouse, plant seeds are sown in flower pots of 12–15 cm diameter. Immediately after sowing, the surface of the soil is treated with an aqueous dispersion or solution of the compounds to be tested. Different concentrations of active ingredient for hectare are employed. The pots are then kept in the greenhouse at 22°–25° C. and 50–70% relative humidity. The test is evaluated 3 weeks later in accordance with the following rating:
1 = plants totally withered
2–8 = intermediate stages of damage
9 = no action (as untreated controls)
— = plant not tested
The results are reported in the following table.

EXAMPLE 7

Postemergence herbicidal action

A large number of weeds and cultivated plants in pots, both monocots and dicots, are sprayed postemergence, in the 4- to 6-leaf stage, with an aqueous active ingredient dispersion at different rates of application,

| | Compound | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| | 2 | | | | 3 | | | | 4 | | | | 5 | | | | 104 | | | | 105 | | | | 108 | | | |
| | Rate of application in kg per hectare | | | | | | | | | | | | | | | | | | | | | | | | | | | |
| Plant | 4 | 2 | 1 | ½ | 4 | 2 | 1 | ½ | 4 | 2 | 1 | ½ | 4 | 2 | 1 | ½ | 4 | 2 | 1 | ½ | 4 | 2 | 1 | ½ | 4 | 2 | 1 | ½ |
| wheat | 1 | 2 | 8 | 9 | 3 | 4 | 8 | 9 | 3 | 3 | 6 | 6 | 2 | 2 | 6 | 6 | 2 | 2 | 3 | 5 | 1 | 1 | 2 | 6 | 2 | 3 | 7 | 8 |
| maize | 2 | 6 | 7 | 8 | 3 | 6 | 9 | 9 | 3 | 3 | 4 | 4 | 4 | 7 | 9 | 9 | 2 | 3 | 7 | 9 | 2 | 5 | 9 | 9 | 4 | 9 | 9 | 9 |
| millet | 6 | 7 | 9 | 9 | 9 | 9 | 9 | 9 | 4 | 7 | 9 | 9 | 4 | 4 | 9 | 9 | 1 | 3 | 4 | 9 | 1 | 2 | 6 | 9 | 6 | 7 | 9 | 9 |
| soybeans | 2 | 2 | 4 | 7 | 4 | 9 | 9 | 9 | 3 | 3 | 8 | 9 | 6 | 7 | 9 | 9 | 1 | 1 | 3 | 7 | 1 | 3 | 7 | 9 | 6 | 7 | 9 | 9 |
| cotton | 18 | — | — | | 9 | 9 | 9 | 9 | 7 | 8 | 9 | 9 | 5 | 9 | 9 | 9 | 5 | 9 | 9 | 9 | 1 | 4 | 9 | 9 | 9 | 9 | 9 | 9 |
| avena fatua | 1 | 1 | 6 | 9 | 2 | 2 | 7 | 8 | 1 | 1 | 1 | 1 | 1 | 1 | 1 | 2 | 1 | 2 | 3 | 7 | 1 | 1 | 2 | 3 | 1 | 1 | 3 | 7 |
| bromus tectorum | 1 | 1 | 5 | 7 | 1 | 2 | 4 | 4 | 1 | 1 | 1 | 2 | 1 | 2 | 2 | 3 | 1 | 2 | 3 | 4 | 1 | 1 | 2 | 7 | 2 | 2 | 4 | 4 |
| lolium perenne | 1 | 2 | 3 | 8 | 2 | 3 | 6 | 7 | 2 | 2 | 3 | 4 | 1 | 2 | 2 | 6 | 1 | 2 | 3 | 5 | 1 | 1 | 1 | 3 | 1 | 1 | 3 | 8 |
| alopecurus myos. | 1 | 2 | 2 | 3 | 2 | 2 | 3 | 9 | 2 | 2 | 2 | 2 | 1 | 1 | 2 | 2 | 2 | 2 | 3 | 9 | 1 | 1 | 3 | 4 | 2 | 2 | 9 | 9 |
| digitaria sang. | 1 | 1 | 2 | 2 | 1 | 1 | 1 | 2 | 1 | 2 | 2 | 2 | 1 | 3 | 8 | 9 | 1 | 1 | 1 | 2 | 2 | 3 | 3 | 4 | 2 | 2 | 7 | 9 |
| echinochloa crus galli | 2 | 2 | 3 | 4 | 3 | 8 | 9 | 9 | 1 | 1 | 1 | 1 | 1 | 2 | 4 | 4 | 1 | 1 | 2 | 3 | 1 | 1 | 2 | 6 | 1 | 2 | 6 | 9 |
| Abu.. | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 2 | 1 | 1 | 3 | 3 |
| sida spinosa | 1 | 1 | 1 | 1 | 1 | 1 | 2 | 3 | 1 | 1 | 1 | 1 | 1 | 1 | 1 | 1 | 1 | 1 | 1 | 1 | 1 | 1 | 1 | 1 | 1 | 1 | 2 | 2 |
| amarantus retroflexus | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 |
| chenopodium album | — | — | — | — | — | — | — | — | — | — | — | — | — | — | — | — | 2 | 2 | 2 | 2 | 1 | 1 | 4 | 4 | 1 | 1 | 1 | 1 |
| solanum nigrum | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 4 | 4 |
| ipomoea purpurea | 1 | 1 | 1 | 3 | 1 | 1 | 9 | 9 | 1 | 1 | 1 | 4 | 1 | 2 | 7 | 9 | 1 | 1 | 1 | 1 | 1 | 1 | 1 | 2 | 1 | 2 | 5 | 9 |
| sinapis alba | 1 | 1 | 1 | 1 | 1 | 1 | 4 | 7 | 1 | 1 | 1 | 1 | 1 | 1 | 1 | 1 | 1 | 1 | 2 | 4 | 1 | 1 | 1 | 1 | 1 | 1 | 1 | 1 |
| stellaria media | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 |
| chrysanthemum leuc. | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 1 |
| Portulacca | 1 | 1 | 1 | 1 | 1 | 1 | 1 | 1 | 1 | 1 | 1 | 1 | 1 | 1 | 1 | 1 | — | — | — | — | — | — | — | — | — | — | — | — |
| kochia scop. | 1 | 1 | 1 | 1 | 1 | 1 | 1 | 1 | 1 | 1 | 1 | 1 | 1 | 1 | 1 | 1 | — | — | — | — | — | — | — | — | — | — | — | — |
| sesbania exaltata | 1 | 1 | 1 | 1 | 1 | 1 | 2 | 9 | 1 | 1 | 1 | 1 | 2 | 7 | 9 | 9 | — | — | — | — | — | — | — | — | — | — | — | — | and then kept at 24°–26° C. and 45–60% relative humidity. The test is evaluated 15 days after treatment.
The reports are reported in the following table.

| | Compound | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|
| | 2 | | | 3 | | | 4 | | | 5 | | | 10 | | | 15 | | | 18 | | | 104 | | | 105 | | | 108 | | | 110 | | |
| | Rate of application in kg per hectare | | | | | | | | | | | | | | | | | | | | | | | | | | | | | |
| Plant | 2 | 1 | ½ | 2 | 1 | ½ | 2 | 1 | ½ | 2 | 1 | ½ | 2 | 1 | ½ | 2 | 1 | ½ | 2 | 1 | ½ | 2 | 1 | ½ | 2 | 1 | ½ | 2 | 1 | ½ |
| barley | 2 | 8 | 9 | 3 | 4 | 9 | 2 | 2 | 2 | 2 | 3 | 7 | 7 | 9 | 9 | 6 | 9 | 9 | 3 | 6 | 9 | 2 | 3 | 9 | 2 | 6 | 8 | 1 | 2 | 3 | 2 | 4 | 6 |
| wheat | 2 | 8 | 9 | 6 | 9 | 9 | 2 | 2 | 3 | 1 | 2 | 7 | 9 | 9 | 9 | 9 | 9 | 9 | 6 | 9 | 9 | 2 | 4 | 9 | 3 | 8 | 9 | 2 | 3 | 8 | 3 | 9 | 9 |
| maize | 6 | 8 | 9 | 3 | 7 | 9 | 2 | 5 | 7 | 2 | 3 | 4 | 9 | 9 | 9 | 9 | 9 | 9 | 6 | 6 | 9 | 6 | 8 | 9 | 5 | 9 | 9 | 4 | 6 | 9 | 2 | 4 | 6 |
| millet | 6 | 9 | 9 | 9 | 9 | 9 | 3 | 7 | 8 | 2 | 3 | 6 | 9 | 9 | 9 | 9 | 9 | 9 | 4 | 7 | 8 | 5 | 7 | 9 | 4 | 9 | 9 | 1 | 4 | 6 | 1 | 6 | 9 |
| soybeans | 2 | 4 | 7 | 2 | 3 | 7 | 3 | 3 | 4 | 3 | 4 | 6 | 3 | 5 | 9 | 7 | 9 | 9 | 2 | 2 | 5 | 2 | 5 | 7 | 1 | 1 | 4 | 1 | 1 | 5 | 1 | 3 | 4 |
| cotton | 1 | 1 | 2 | 2 | 4 | 7 | 2 | 2 | 2 | 1 | 1 | 2 | 8 | 9 | 9 | 7 | 8 | 9 | 6 | 8 | 9 | 8 | 9 | 9 | 2 | 7 | 8 | 2 | 2 | 2 | 2 | 2 | 6 |
| avena fatua | 1 | 2 | 3 | 1 | 7 | 9 | 1 | 1 | 1 | 1 | 1 | 4 | 1 | 3 | 9 | 2 | 8 | 9 | 2 | 3 | 9 | 1 | 2 | 4 | 1 | 3 | 9 | 1 | 2 | 9 | 1 | 1 | 8 |
| bromus tectorum | 1 | 2 | 3 | 4 | 5 | 5 | 2 | 5 | 6 | 2 | 2 | 2 | 9 | 9 | 9 | 9 | 9 | 9 | 5 | 7 | 9 | 2 | 3 | 4 | 1 | 2 | 3 | 2 | 2 | 9 | 2 | 4 | 9 |
| lolium perenne | 2 | 3 | 5 | 3 | 4 | 9 | 1 | 2 | 2 | 1 | 2 | 3 | 7 | 8 | 9 | 9 | 9 | 9 | 5 | 7 | 9 | 2 | 3 | 6 | 1 | 3 | 6 | 2 | 4 | 7 | 2 | 2 | 4 |
| alopecurus myos. | 1 | 2 | 3 | 2 | 3 | 4 | 1 | 1 | 1 | 1 | 1 | 2 | 1 | 1 | 6 | 2 | 2 | 8 | 2 | 2 | 4 | 2 | 2 | 4 | 1 | 2 | 4 | 1 | 1 | 3 | 2 | 2 | 4 |
| digitaria sang. | 1 | 1 | 2 | 2 | 2 | 2 | 1 | 1 | 1 | 1 | 1 | 2 | 1 | 2 | 9 | 2 | 3 | 9 | 2 | 2 | 3 | 2 | 4 | 5 | 1 | 2 | 3 | 1 | 1 | 6 | 1 | 2 | 4 |
| echinochloa crus galli | 1 | 2 | 3 | 1 | 6 | 7 | 1 | 1 | 1 | 1 | 1 | 2 | 1 | 9 | 9 | 2 | 7 | 9 | 2 | 2 | 4 | 2 | 3 | 6 | 1 | 2 | 4 | 1 | 2 | 2 | 1 | 2 | 4 |
| Abutilon | 1 | 1 | 1 | 1 | 1 | 1 | 1 | 1 | 1 | 1 | 1 | 1 | 2 | 2 | 4 | 1 | 4 | 6 | 1 | 2 | 2 | 1 | 1 | 4 | 1 | 1 | 4 | 1 | 1 | 1 | 1 | 2 | 4 |
| sida spinosa | 1 | 1 | 1 | 1 | 1 | 1 | 1 | 3 | 6 | 1 | 1 | 2 | 2 | 3 | 3 | 1 | 4 | 6 | 1 | 4 | 6 | 1 | 1 | 6 | 2 | 2 | 3 | 1 | 2 | 3 | 1 | 2 | 3 |
| Xanthium | — | — | — | — | — | — | — | — | — | — | — | — | 2 | 3 | 3 | 1 | 6 | 9 | 1 | 1 | 1 | 1 | 1 | 2 | 1 | 1 | 1 | 1 | 1 | 5 | 1 | 1 | 1 |
| amaranthus retrofl. | 1 | 1 | 1 | 1 | 1 | 1 | 1 | 1 | 1 | 1 | 1 | 1 | 1 | 2 | 3 | 1 | 1 | 1 | 1 | 1 | 1 | 1 | 1 | 1 | 1 | 1 | 3 | 1 | 1 | 1 | 1 | 1 | 1 |
| chenopodium | — | — | — | — | — | — | — | — | — | — | — | — | 1 | 1 | 1 | 1 | 1 | 3 | 1 | 6 | 7 | 1 | 1 | 1 | 2 | 6 | 9 | 1 | 1 | 1 | 1 | 1 | 1 |

-continued

| | Compound | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|
| | 2 | | | 3 | | | 4 | | | 5 | | | 10 | | | 15 | | | 18 | | | 104 | | | 105 | | | 108 | | | 110 | | |
| | Rate of application in kg per hectare | | | | | | | | | | | | | | | | | | | | | | | | | | | | | | |
| Plant | 2 | 1 | ½ | 2 | 1 | ½ | 2 | 1 | ½ | 2 | 1 | ½ | 2 | 1 | ½ | 2 | 1 | ½ | 2 | 1 | ½ | 2 | 1 | ½ | 2 | 1 | ½ | 2 | 1 | ½ | 2 | 1 | ½ |
| *album* | | | | | | | | | | | | | | | | | | | | | | | | | | | | | | | | | |
| *solanum nigrum* | 1 | 1 | 1 | 1 | 1 | 1 | 1 | 1 | 1 | 1 | 1 | 1 | 1 | 1 | 1 | 1 | 1 | 1 | 1 | 1 | 1 | 1 | 2 | 3 | 1 | 1 | 1 | 1 | 1 | 1 | 1 | 1 | 1 |
| *ipomoea purpurea* | 1 | 1 | 3 | 2 | 3 | 8 | 1 | 2 | 2 | 1 | 1 | 3 | 1 | 3 | 8 | 2 | 7 | 9 | 1 | 2 | 3 | 1 | 2 | 3 | 1 | 1 | 1 | 1 | 1 | 2 | 1 | 1 | 1 |
| *sinapis alba* | 1 | 1 | 1 | 1 | 1 | 3 | 1 | 1 | 1 | 1 | 1 | 1 | 1 | 1 | 6 | 1 | 1 | 3 | 1 | 1 | 1 | 1 | 1 | 2 | 1 | 1 | 1 | 1 | 1 | 1 | 1 | 1 | 1 |
| *stellaria media* | 1 | 1 | 1 | 1 | 1 | 1 | 1 | 1 | 1 | 1 | 1 | 1 | 1 | 1 | 2 | 1 | 2 | 2 | 1 | 1 | 2 | 1 | 1 | 1 | 1 | 1 | 1 | 1 | 1 | 1 | 1 | 1 | 2 |
| *chrysanthemum leuc.* | 1 | 1 | 1 | 1 | 1 | 1 | 1 | 1 | 1 | 1 | 1 | 1 | 1 | 1 | 1 | 1 | 7 | 7 | 1 | 1 | 2 | 1 | 1 | 1 | 1 | 1 | 4 | 1 | 1 | 1 | 1 | 1 | 1 |
| *galium aparine* | 1 | 2 | 2 | 9 | 9 | 9 | 6 | 7 | 9 | 1 | 1 | 1 | 7 | 9 | 9 | 2 | 6 | 9 | 1 | 7 | 9 | 2 | 9 | 9 | 1 | 1 | 1 | 1 | 1 | 2 | 2 | 9 | 9 |
| *viola tricolor* | — | — | — | — | — | — | — | — | — | — | — | — | 1 | 1 | 9 | 2 | 3 | 9 | 4 | 7 | 8 | 1 | 2 | 6 | 1 | 1 | 2 | 1 | 1 | 1 | 2 | 3 | 6 |
| Veronica | — | — | — | — | — | — | — | — | — | — | — | — | 1 | 4 | 8 | 1 | 1 | 3 | 1 | 1 | 3 | 1 | 1 | 9 | 1 | 1 | 1 | 1 | 1 | 1 | 1 | 1 | 1 |
| Portulacca | 1 | 1 | 1 | 1 | 1 | 1 | 1 | 1 | 1 | 1 | 1 | 1 | — | — | — | — | — | — | — | — | — | — | — | — | — | — | — | — | — | — | — | — | — |
| *kochi scop.* | 1 | 1 | 1 | 1 | 1 | 1 | 1 | 1 | 1 | 1 | 1 | 1 | — | — | — | — | — | — | — | — | — | — | — | — | — | — | — | — | — | — | — | — | — |
| *sesbania exalt.* | 1 | 1 | 1 | 1 | 1 | 1 | 1 | 1 | 1 | 1 | 1 | 1 | — | — | — | — | — | — | — | — | — | — | — | — | — | — | — | — | — | — | — | — | — |

EXAMPLE 8

Desiccation and defoliation action

Cotton plants of the variety Deltapine are reared in earthenware pots in a greenhouse. After the first capsules have formed, the plants are sprayed with aqueous formulations of compounds 1 and 2 at a rate of application corresponding to 1, 2, 0.6 and 0.3 kg/ha respectively in field application. Untreated plants act as controls. Evaluation of the test is made 3, 7 and 14 days after application of the active ingredient by determining the degree of defoliation (percentage of fallen leaves) and of desiccation (drying out of the leaves remaining on the plant). Plants treated with compounds 1, 2, 7, 104, 108 and 110 at rates of application of 1.2 and 0.6 kg/ha are left after 2 weeks with only a few dried out leaves.

Growth regulation and yield increase in soybeans

Soybeans of the "Hark" variety are sown in plastic containers in an earth/turf/sand mixture (6:3:1) in a climatic chamber in a greenhouse. By means of an optimum control of temperature, watering and lighting, as well as by addition of fertiliser, plants in the 5–6 trefoil leaf stage are able to develop after about 5 weeks. At this time the plants are sprayed with aqueous mixtures of an active ingredient in concentrations of 10, 50, 100 and 500 ppm until they are dripping wet. The plants are then further reared in the greenhouse and the test is evaluated 5 weeks after treatment. Compared with untreated controls, 10 soybean plants treated with compound 6 at rates of application of 50 and 100 ppm exhibited the following features:

a respective increase in weight of the harvested siliques of 3 to 17%, a reduction of the growth in height of 9 and 14% respectively, an average growth of sucker formation of 5–11%.

What is claimed is:

1. A thiocarbamoylalkoxyphenylurea of the formula

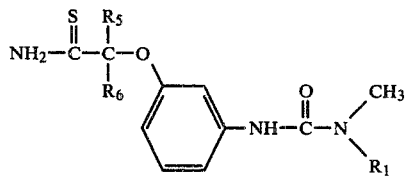

wherein

R$_1$ is methyl or methoxy,

R$_5$ is hydrogen, C$_1$–C$_4$ alkyl, C$_1$–C$_4$ alkoxy or C$_2$–C$_5$ alkoxyalkyl, and R$_6$ is hydrogen or C$_1$–C$_4$ alkyl.

2. α-[m-(3-Methoxy-3-methylureido)phenoxy]thiopropionamide according to claim 1.

3. α-[m-(3,3-Dimethylureido)phenoxy]thioisobutyramide according to claim 1.

4. α-[m-(3-methoxy-3-methylureido)phenoxy]thioisobutyramide according to claim 1.

5. α-[o-chloro-p-(3,3-dimethylureido)phenoxy]thio-n-butyramide.

* * * * *